United States Patent [19]

Sudo et al.

[11] Patent Number: 4,746,212
[45] Date of Patent: May 24, 1988

[54] BOTTLE CAP INSPECTION APPARATUS

[75] Inventors: Masao Sudo, Kawaguchi; Toshiyuki Shimizu, Funabashi, both of Japan

[73] Assignee: Hajime Industries Ltd., Tokyo, Japan

[21] Appl. No.: 843,158

[22] Filed: Mar. 24, 1986

[30] Foreign Application Priority Data

Mar. 29, 1985 [JP] Japan .................................. 60-65585

[51] Int. Cl.$^4$ ............................................ G01N 21/90
[52] U.S. Cl. ................... 356/240; 250/223 B
[58] Field of Search .............................. 356/237, 240; 250/223 B

[56] References Cited

U.S. PATENT DOCUMENTS 4,606,635 8/1986 Miyazawa et al. ................. 356/240

FOREIGN PATENT DOCUMENTS 201241 10/1985 Japan .................................. 356/237

Primary Examiner—Davis L. Willis
Assistant Examiner—Matthew W. Koren
Attorney, Agent, or Firm—Murray Schaffer

[57] ABSTRACT

A bottle cap inspection apparatus having a circular shaped light source which is placed to irradiate a cap on a bottle mouth from above; a photoelectric conversion sensor above the cap for receiving the light reflected from the cap; and, an electronic processor for processing an electrical signal from the photoelectric conversion sensor to detect defects in the cap. The bottle is placed under the photoelectric conversion sensor in a manner such that the center axis of the bottle coincides with the optical axis of the photoelectric conversion sensor, and the center of the circular light source coincides with the optical axis. An optical mask is located between the light source and the cap on the bottle mouth such that it defines an outer peripheral surface of a visual field of the photoelectric conversion sensor looking at the bottle mouth as well as an inner peripheral surface of the irradiation range onto the bottle mouth from the circular light source as different conical shapes. A portion of the bottle mouth cap to be inspected is located in a vicinity of the crossing portion of the outer peripheral surface of the conical shaped visual field of the photoelectric conversion sensor with the inner peripheral surface of the irradiation range of the circular light source.

2 Claims, 3 Drawing Sheets

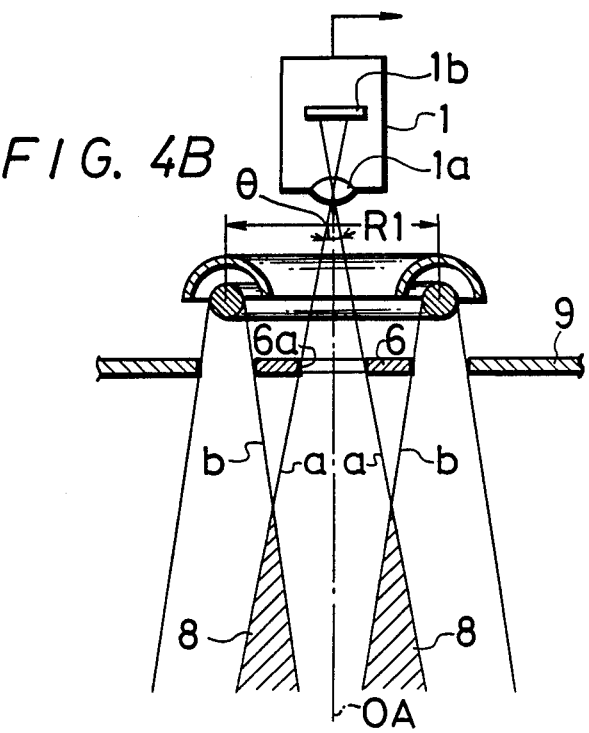
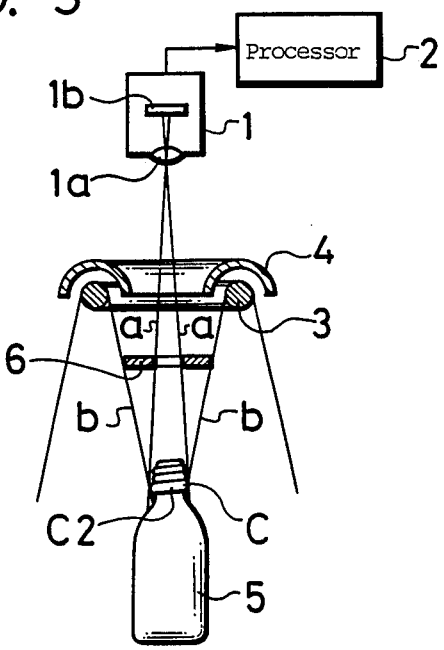
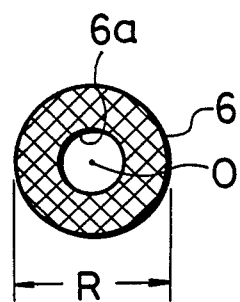

BOTTLE CAP INSPECTION APPARATUS

BACKGROUND OF THE INVENTION

1. Field of the Invention

The present invention relates generally to an inspection apparatus for bottle mouth caps, and is directed more specifically to an inspection apparatus which automatically detects the good or bad of screw-on caps by using photoelectric conversion sensors and electrical processors such as a computer or the like.

2. Description of the Prior Art

There are a wide variety of capping methods as well as kinds of caps that are used for bottled products such as spirits, beverages or other fluids. For instance, there are the plug-in type cap that inserts a cork or plastic material into the bottle mouth; or, the screw type wherein the outside of the bottle mouth is formed with a screw thread to which a cap made of metal or plastic that has a threaded screw is screwed thereon. Both types are equally used even for the recycled bottles (e.g., recovered and refilled) in which cases the same bottles are repeatedly used.

On the other hand, the method of using recycled or refilled bottles faces problems such as increases in recovery related costs, as well as the bottle breakages during the market cycle. Consequently, there is a noted increase in the use of the so-called one way bottles which are only used one time, during the recent years.

This trend is not only true for large sized bottles, but can generally be seen in the smaller sized bottles. As a result, the concept relating to the construction of the cap on these one way bottles differs somewhat from the case of the recycle type bottles. That is, in the first place, the cap must be easily openable by hand, and in the second place, the cap must have such a construction that it can be tightly secured onto the bottle mouth and will not easily open until the bottle arrives in the hands of the final user or client.

FIG. 1 shows a side view of one example of a cap C that has such a construction. Further, the cap C is made of metal material as one example. As shown on the same figure, cap C has a screw thread portion C1 which screws on to the screw portion formed on the outer periphery of the bottle mouth, (not shown on the drawing). Continuing from the lower edge of the screw portion C1, there is provided a ring like lower portion C2 that is tightened on to the lower part of the bottle mouth, after the cap C is screwed on to the bottle mouth. When the cap C that is screwed on the bottle mouth is turned in the direction to be un-screwed and taken off, cap C easily detaches from the bottle mouth. However, the lower portion C2 of the cap C contains such a taper that it is larger in diameter going upwards from its lowest edge, and is smaller in diameter as it goes further upwards from its maximum protruding portion. When the cap C is screwed on to the bottle mouth, its lower portion C2 is tightened on to the lower protruding part of the mouth so that it prevents the cap C from loosening as a result of general vibration and the like during shipment and hence the content fluid inside the bottle does not leak away from the bottle mouth, or the cap C cannot detach itself from the bottle mouth.

When the final user of the bottle takes off the cap C, a slight force is applied to the cap C at the start causing the cap C to unscrew. A subsequent force to cause the cap to come off of the bottle mouth is applied to the lower portion C2 of the cap C which remains tightened on the bottle. Since scores (or notches) which will be described later are formed in the lower portion C2, the lower portion C2 is only partially broken from the cap C along some of the scores, after which the cap C easily rotates so that the cap C can be detached from the bottle mouth. To permit the cap C to be easily detached and removed from the bottle mouth, a plurality of horizontal scores C3 are engraved at a predetermined distance along the circumference of the maximum protruding portion of the lower portion C2, and/or connected to such horizontal scores C3, a plurality of vertical direction running scores C4 at a predetermined distance are engraved respectively. Needless to say, the number or sequence of the scores C3 and C4 may vary depending upon the kinds of purposes desired for them.

From a psychological standpoint, when the end user takes the bottle in his hand and visually checks the lower portion C2 of the cap C to confirm that there is no damaged part in the scores C3 or C4, a positive feeling is generated of reliance upon the bottled product. This type of cap C is normally called as the Pilfer Proof Cap (or abbreviated as the PP Cap).

The lower portion of the cap C that is shown on FIG. 1 illustrates that the scored portion C2 is a good product without defects. On the other hand, FIGS. 2A and 2B illustrate an example, with partial magnification of side and top views, where there is a defect in the scored portion C2. In other words, as shown on FIGS. 2A and 2B, one piece C5 between vertical neighbouring scores C4 of the scored portion C2 of cap C has come apart, at one of the vertical scores C4, from the scored portion C2 and protrudes towards the outside of the cap C.

It is, therefore, essential for the maker or bottler that he confirm, after filling the one way bottles with fluid and screwing the above mentioned cap on to the bottle mouth, firstly that the cap does not permit leakage of the fluid and secondly, to especially check whether or not any damage and/or abnormally exist at the scored portion of the cap.

It is now considered as a natural necessity to automate and achieve material labour savings in inspection process in the same manner as automation obtains labour savings advancements in the various production processes.

In relation to inspection automation, various proposals are conventionally made using a variety of sensor types. In one such case, a method to automatically inspect the lower part of a bottle cap is attempted by irradiating light onto the lower part of the cap, from which the reflected light is caught by a photoelectric conversion sensor, detecting the existence of any abnormality in the cap.

However, as mentioned, the lower part of cap C (i.e., the section C2) carrying the score structure, is located lower than the top surface of the bottle mouth. The top surface extends all around the outer periphery of the bottle mouth and at the same time forms one part of the cap C, which further is curved inwardly and downwardly to the lowest edge, so that the inspection of this part in one shot cannot be easily made.

OBJECTS AND SUMMARY OF THE INVENTION

Accordingly, it is an object of the present invention to provide a novel inspection apparatus for a bottle mouth cap.

It is another object of the present invention to provide an inspection apparatus which can automatically inspect the bottle mouth cap.

It is a further object of the present invention to provide an inspection apparatus for a bottle mouth cap which uses a photoelectric conversion sensor to detect a defect on the lower portion of a screwed-in type bottle mouth cap positively and one that has a simple structure.

According to an aspect of the present invention, there is proposed a bottle cap inspection apparatus which comprises:

(a) a circular shaped light source which is located to irradiate the cap on a bottle mouth from above;

(b) a photoelectric conversion sensor located above the cap for receiving the light reflected from the cap;

(c) an electronic processor for processing an electrical signal from the photoelectric conversion sensor to detect defects of said cap; wherein the bottle is placed under the photoelectric conversion sensor in a manner that the center axis of the bottle coincides with the optical axis of the photoelectric conversion sensor, and the center of the circular light source coincides with the optical axis; and (d) an optical mask is located between the light source and the cap such that it defines an outer peripheral surface of a visual field of said photoelectric conversion sensor looking at said bottle mouth as well as an inner peripheral surface of the irradiation range onto said bottle mouth from the circular light source as different conical shapes. A portion of the bottle mouth cap to be inspected is located in the vicinity of the crossing portion of the outer peripheral surface of the conical shaped visual field of the photoelectric conversion sensor with the inner peripheral surface of the irradiation range of the circular light source.

Additional and other objects, features and advantages of the present invention will become apparent from the following description taken in conjunction with the accompanying drawings through which like references designate the same elements and parts.

BRIEF DESCRIPTION OF THE DRAWINGS

FIG. 3 is a schematic diagram with a partial cross section view of this bottle and cap illustrating one example of the present invention;

FIG. 4A is a plan view of the mask used in the example of FIG. 3;

FIG. 4B is an enlarged view of FIG. 3;

DESCRIPTION OF THE PREFERRED EMBODIMENTS

Figure 1:
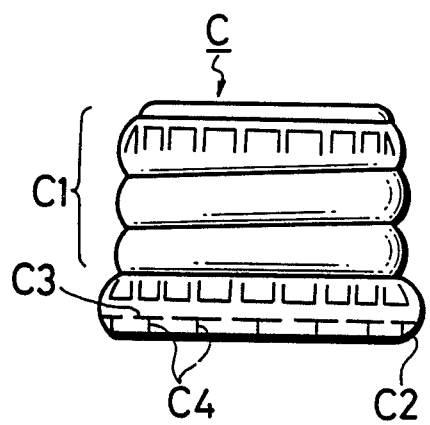
FIG. 1 is a side elevational view of a screw-on type cap as one example of the objects which may be inspected.

The present invention will be explained hereunder in reference with the attached drawings.

FIG. 3 illustrates the entire setup of one example of the present invention comprising a photoelectric conversion sensor 1 such as a television camera having an optical system 1a, for instance, a lens that is used to photosense an object to be inspected, and a photoelectric conversion screen 1b where the image of the inspected object is formed.

A processor 2, (electric processor) such as a computer or the like is provided to process the electrical signal that corresponds to the image of the inspected object, as produced by the photoelectric conversion sensor 1. Processing may be carried out, for instance, by comparing the produced signal with an electrical signal that corresponds to a good product thereby determining the good or bad of the inspected object. A circular shaped light source 3 such as a circuline lamp uniformly irradiates the inspected object from above and is placed between the inspected object and the photoelectric conversion sensor 1. A circular shaped reflection plate 4 capable of raising the irradiation efficiency from the light source 3 and at the same time serving to prevent unnecessary light from the light source 3 to directly enter the photoelectric conversion sensor 1, is placed between the photoelectric conversion sensor 1 and the light source 3. In this example, a bottle 5 having the object cap C screwed tightly on its mouth is placed under the light source 3 so that the upper surface of the cap C faces the photoelectric conversion sensor 1. An optical mask 6 is placed between the cap C and the light source 3.

The structure and function of the example of the optical mask 6 is shown with reference to FIGS. 4A and 4B. As shown in FIG. 4A, the optical mask 6 comprises a ring like disc made of an opaque material having at its center O a concentric aperture 6a.

Needless to say, instead of an opaque disc having a through-hole 6a, a transparent material may be employed and selectively rendered opaque to light except for a central light passage, providing an annular ring like mask.

In the same figure, the opaque portion of the optical mask 6 is indicated by cross hatchings. As shown in FIG. 4B, the optical mask 6 is placed under the circular light source 3 in a manner that its plate surface is substantially perpendicular to the optical axis OA of the lens 1a of the photoelectric conversion sensor 1. At the same time the center O of the aperture 6a is generally aligned with the optical axis OA. Further, the outer diameter R of the optical mask 6 is made smaller than the diameter R1 of the circular light source 3 and the center of the light source 3 is placed to match the optical axis OA and have its plane substantially perpendicular to the optical axis OA.

As shown in FIG. 4B, when all of the above components are properly arranged, the visual field of the photoelectric conversion sensor 1 and hence that of its lens 1a is confined within the solid angle $\theta$ by the aperture 6a of the optical mask 6. In other words, the outer peripheral surface of the visual field of photoelectric conversion sensor 1 is defined by the outer peripheral surface of the cone that is formed by rotating a straight line a that passes through the center of the lens 1a and the lower inner edge of the through-hole 6a with the optical axis OA as its central axis.

On the other hand, the inner circumference surface of the visual field formed by the irradiating range of the circular light source 3 is defined by the outer peripheral surface of an oppositely directed cone formed by rotating a straight line b extending from the inside edge of the circular light source 3 and outer edge of the disc-shaped optical mask 6 around the optical axis OA as the central axis.

In other words, the irradiation range 8 against cap C from the circular light source 3 will be created by the overlapping cones, and is shown in FIG. 1b by the cross-hatching.

In the present invention, the photoelectric conversion sensor 1 will receive the light reflected from the lower portion C2 of the cap C on bottle 5 when the inspected object is placed in the range 8 where the light from the light source 3 arrives. The visual field of the lens 1a contains the crosshatched section, and all reflected light from this region will be able to reach the photoelectric conversion sensor 1. That is to say, the entire crosshatched range 8 forms a possible inspection region in accordance with the invention as shown on FIG. 3 and FIG. 4.

Figure 2A:
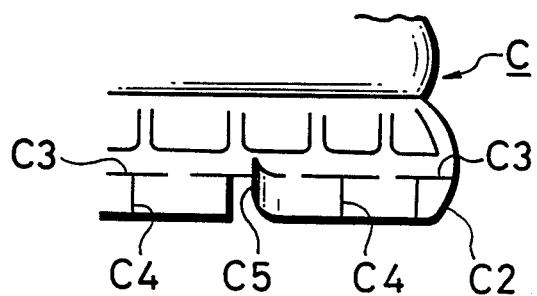
FIG. 2A is a partial, enlarged elevational view of a defective cap.
Figure 2B:
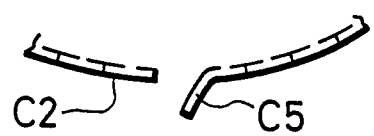
FIG. 2B is a partial, enlarged top view of the cap.
Figure 5:
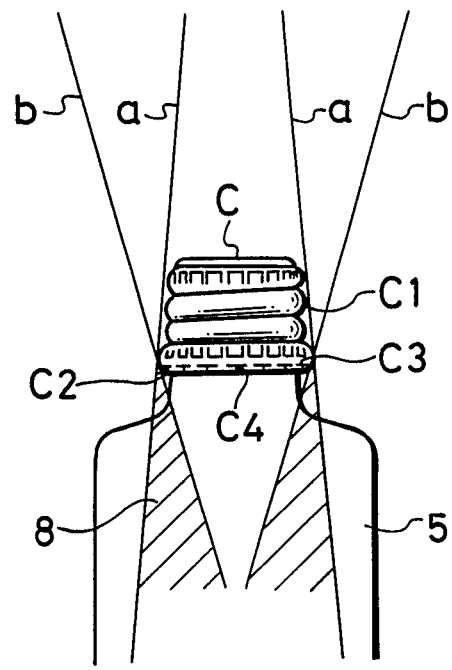
FIG. 5 is an elevational view of bottle and cap to show the placing of the object to be inspected in the irradiation range.

On the other hand, since the present invention is not intended to inspect the entire cap C, but rather only the lower portion C2 of cap C as shown on FIGS. 1 and 2, the bottle 5 is located such that only this scored portion C2 lies in the possible inspection range marked by crosshatched lines as indicated as symbol 8 in FIG. 4. This can be effected, as shown in FIG. 5, by placing the circular crossing edge between the outer peripheral surface of the visual field of photoelectric conversion sensor 1 and the inner peripheral surface of the conical irradiation range of the circular light source 3, i.e., the crossing point between the lines a and b, at the maximum protruding portion (the portion at which score C3 is formed) which is the lowest portion C2 of the cap C. By positioning cap C in this way, the higher level screw portion C1 comes within the visual field of the photoelectric conversion sensor 1, but the light from the light source 3 does not impinge thereon but arrives only on the scored portion C2 of cap C, which is the sole portion to be inspected.

At this time, due to the fact that, the scored portion C2 is tapered in shape so that the diameter gets smaller as it extends downwardly from the maximum protruding part at which the score C3 is formed, the light from the light source 3 as shown by straight line b, approximately runs in line with the tapered surface. Therefore, unless there is a defect at the scored portion C2, the reflected light thereon only advances downwards and is not reflected upward so that it does not reach the photoelectric conversion sensor 1. However, as shown with the example at FIG. 2, when there is a defect at the scored portion C2, such as the part C5 broken or bent outwards, the light reflected therefrom travels upwardly within the visual field of the photoelectric conversion sensor 1. Therefore, with the function of processor 2, it can be detected that this cap C is a defective product.

In this case, it is noted that on FIG. 4B, 9 is a light shield plate which is used to shield unnecessary light from interfering with the flaw detection system.

Figure 6:
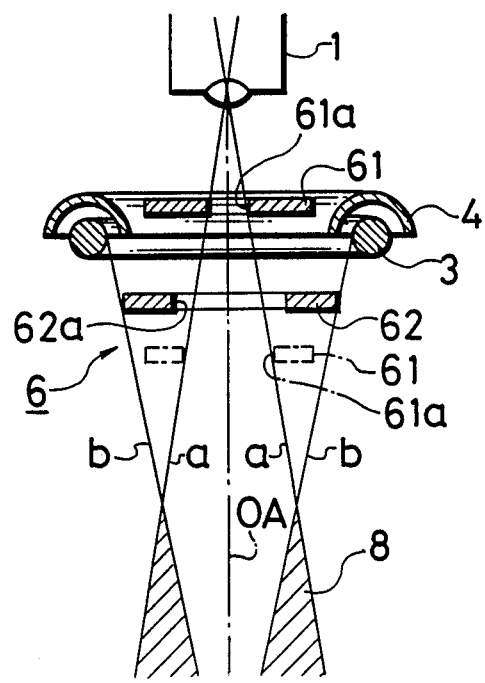
FIG. 6 illustrates an enlarged cross section view of the main portion of another example of the present invention.

FIG. 6 is a schematic view illustrating the main part of another example of the present invention. In this example, the optical mask 6 comprises two optical masks 61 and 62. Optical mask 61 is made of an opaque thin plate in same manner as the previous example, and as to control only the visual field of the photoelectric conversion sensor 1, it has a light passage portion or a through-hole 61a at its center. The other optical mask 62 is a round plate or disc made of opaque material that has the outer edge so that the irradiation range from light source 3 is similarly controlled as in the previous example. Further, in this example, since the optical mask 62 is placed under the optical mask 61, it also has a through-hole 62a at its center so as not to interfere with the visual field of photoelectric conversion sensor 1 as controlled by optical mask 61.

While the optical mask 61 is placed above the optical mask 62, as shown with a broken line in FIG. 6, it may be placed under the optical mask 62. In such case, it is needless to say that the diameter of its through-hole 61a must not only be enlarged to respond with the visual field of the photoelectric conversion sensor 1 as shown in FIG. 6, but the outer peripheral edge of the optical mask 61 must be made in a round shape and the diameter thereof must be smaller than the inner diameter of the irradiated range of light source 3.

Further, in each of the aforementioned examples, it is needless to say that the distance between the photoelectric conversion sensor 1 and cap C, the diameter of the circular light as source 3, the diameters of the optical masks 6, 61, 62 as well as the diameters of the through-holes thereof respectively such as 6a, 61a, 62a as well as their relative positions, all may be properly changed in response to the dimension and shapes of the inspected portions of cap C on bottles.

As described above, the visual field of the photoelectric conversion sensor 1 and the irradiation range of the circular light source 3 or its inner peripheral surface are defined by the special optical mask 6 and so on to thereby form the region for possible inspection. Then the bottle 5 is placed at the specific position within the above region, where the portion of cap C or the scored portion C2 thereof are irradiated by the light source 3 at the same time. Only when there is a defect on that portion is the reflected light thereon received by the photoelectric conversion sensor 1. Therefore, all the ring-shaped scored portion C2 of cap C, which is the object to be inspected, can be automatically inspected at the same time with high accuracy without rotating the cap C, and/or bottle 5.

Further, one example of the optical mask, which is one of the main elements of the present invention, is a disc made of opaque material and formed in such a manner that there is bored at the center of the disc, for example, an aperture with a predetermined diameter to define the visual field of the photoelectric conversion sensor and the outer peripheral edge of the disc is shaped to define the inner peripheral surface of the irradiation range of the light from the light source. Thus, the present invention can be made at low cost.

Also, since it is sufficient that the photoelectric conversion sensor generates, for example, an electrical signal only when it receives reflected light, and this sensor and the processor may be simple in structure, they can positively and accurately detect the defect.

Further, shown in FIG. 6, since the optical mask is formed of the optical mask 61 which defines the visual field of the photoelectric conversion sensor 1 and of the optical mask 62 which defines the irradiation range of the light source 3, if the respective optical masks are moved along the optical axis OA, the position of the possible inspection region can be changed easily.

The above description is given on a single preferred embodiment of the invention but it will be apparent that many modifications and variations could be effected by one skilled in the art without departing from the spirits or scope of the novel concepts of the invention so that the scope of the invention should be determined by the appended claims only.

We claim as our invention:

1. A bottle cap inspection apparatus comprising:
   (a) a circular shaped light source which is placed to irradiate a cap on a bottle mouth from its above;
   (b) a photoelectric conversion sensor placed above said cap for receiving a reflected light on said cap;
   (c) an electronic processor for precessing an electrical signal from said photoelectric conversion sensor to inspect defects of said cap;
   said bottle being placed under said photoelectric conversion sensor in a manner that the center axis of said bottle coincides with an optical axis of said photoelectric conversion sensor, the center of said circular light source coinciding with said optical axis; and
   (d) an optical mask comprising a disc made of opaque material having at its center a concentric throughhole defining the outer peripheral surface of the conical shaped visual field of said photoelectric conversion sensor, and an outer peripheral edge defining the inner peripheral surface of the conical shaped irradiation range of said circular light source, said mask being located between said light source and said cap on the bottle mouth such that it defines an outer peripheral surface of a visual field of said photoelectric conversion sensor looking at said bottle mouth as well as an inner peripheral surface of the irradiation range onto said bottle mouth from said circular light source as different conical shapes, a portion of the said bottle mouth cap to be inspected being located in a vicinity of a crossing portion of the outer peripheral surface of the conical shaped visual field of said photoelectric conversion sensor with the inner peripheral surface of the irradiation range of said circular light source.

2. A bottle cap inspection apparatus comprising:
   (a) a circular shaped light source which is placed to irradiate a cap on a bottle mouth from its above;
   (b) a photoelectric conversion sensor placed above said cap for receiving a reflected light on said cap;
   (c) an electronic processor for processing an electrical signal from said photoelectric conversion sensor to inspect defects of said cap;
   said bottle being placed under said photoelectric conversion sensor in a manner that the center axis of said bottle coincides with an optical axis of said photoelectric conversion sensor, the center of said circular light source coinciding with said optical axis; and
   (d) an optical mask comprising formed of a first optical member which defines the outer peripheral surface of the conical shaped visual field of said photoelectric conversion sensor and a second optical member which defines the inner surface of the conical shaped irradiation range of said circular source said mask being located between said light source and said cap on the bottle mouth such that it defines an outer peripheral surface of a visual field of said photoelectric conversion sensor looking at said bottle mouth as well as an inner peripheral surface of the irradiation range onto said bottle mouth from said circular light source as different conical shapes, a portion of the said bottle mouth cap to be inspected being located in a vicinity of a crossing portion of the outer peripheral surface of the conical shaped visual field of said photoelectric conversion sensor with the inner peripheral surface of the irradiation range of said circular light source.

* * * * *